(12) United States Patent
Lyren

(10) Patent No.: US 10,265,143 B1
(45) Date of Patent: *Apr. 23, 2019

(54) DENTAL IMPLANT WITH AN INTERFACE THAT CONNECTS A POROUS BONE FIXATION BODY TO A METAL CORONAL BODY

(71) Applicant: Four Mile Bay, LLC, Wadsworth, OH (US)

(72) Inventor: Philip Scott Lyren, Hong Kong (CN)

( * ) Notice: Subject to any disclaimer, the term of this patent is extended or adjusted under 35 U.S.C. 154(b) by 311 days.

This patent is subject to a terminal disclaimer.

(21) Appl. No.: 15/143,511

(22) Filed: Apr. 30, 2016

Related U.S. Application Data

(63) Continuation of application No. 14/880,234, filed on Oct. 11, 2015, now Pat. No. 9,351,813, which is a continuation of application No. 14/164,240, filed on Jan. 26, 2014, now Pat. No. 9,271,811, which is a continuation of application No. 13/571,375, filed on Aug. 10, 2012, now Pat. No. 8,684,734, which is a continuation-in-part of application No. 13/195,872, filed on Aug. 2, 2011, now Pat. No. 8,297,974, which is a continuation of application No. 11/358,375, filed on Feb. 21, 2006, now Pat. No. 8,043,090, which is a continuation of application No. 10/375,343, filed on Feb. 27, 2003, now Pat. No. 7,291,012.

(51) Int. Cl.
*A61C 8/00* (2006.01)
*A61C 8/02* (2006.01)

(52) U.S. Cl.
CPC ............ *A61C 8/0037* (2013.01); *A61C 8/006* (2013.01); *A61C 8/0006* (2013.01); *A61C 8/0012* (2013.01); *A61C 8/0054* (2013.01); *A61C 8/0018* (2013.01); *A61C 2008/0046* (2013.01); *Y10T 29/49567* (2015.01)

(58) Field of Classification Search
CPC ... A61C 8/0006; A61C 8/0012; A61C 8/0018; A61C 8/0024; A61C 8/0039; A61C 2008/0046; A61C 8/0037; A61C 8/006; A61C 8/0054; A61L 27/56; A61L 27/3865; A61L 27/06
USPC .......................... 29/896.1; 623/16.11, 17.17; 433/173–176
See application file for complete search history.

(56) References Cited

U.S. PATENT DOCUMENTS

| | | | | |
|---|---|---|---|---|
| 4,957,819 A | * | 9/1990 | Kawahara | A61C 8/0012 428/547 |
| 5,002,488 A | * | 3/1991 | Homsy | A61C 8/0012 433/169 |
| 5,049,074 A | * | 9/1991 | Otani | A61C 8/0012 433/173 |
| 5,282,861 A | * | 2/1994 | Kaplan | A61F 2/28 623/23.51 |
| 5,383,935 A | * | 1/1995 | Shirkhanzadeh | A61C 8/00 433/173 |
| 6,095,817 A | * | 8/2000 | Wagner | A61C 8/0012 433/173 |

(Continued)

*Primary Examiner* — Sarang Afzali

(57) ABSTRACT

A dental implant has a coronal body formed of solid metal that connects at an interface to a bone fixation body. The bone fixation body is made separately from the coronal body and has a porous structure with a cylindrical shape. The bone fixation body connects to the coronal body after the bone fixation body is separately made from the coronal body.

7 Claims, 5 Drawing Sheets

(56) References Cited

U.S. PATENT DOCUMENTS

| | | | |
|---|---|---|---|
| 8,297,974 B1* | 10/2012 | Lyren | A61C 8/0018 433/173 |
| 8,684,734 B1* | 4/2014 | Lyren | A61L 27/06 433/173 |
| 9,271,811 B1* | 3/2016 | Lyren | A61L 27/06 |
| 9,351,813 B1* | 5/2016 | Lyren | A61L 27/06 |
| 2009/0011384 A1* | 1/2009 | Collins | A61C 8/0012 433/174 |
| 2009/0036908 A1* | 2/2009 | Zokol | A61B 17/60 606/151 |
| 2009/0061387 A1* | 3/2009 | Lomicka | A61C 8/0012 433/173 |
| 2009/0061388 A1* | 3/2009 | Collins | A61C 8/0006 433/174 |

* cited by examiner

DENTAL IMPLANT WITH AN INTERFACE THAT CONNECTS A POROUS BONE FIXATION BODY TO A METAL CORONAL BODY

CROSS-REFERENCE TO RELATED APPLICATIONS

This application is a continuation of U.S. patent application having Ser. No. 14/880,234 filed on 11 Oct. 2015, which is a continuation of U.S. patent application having Ser. No. 14/164,240 filed on 26 Jan. 2014, now U.S. Pat. No. 9,271,811, which is a continuation of U.S. patent application having Ser. No. 13/571,375 filed on 10 Aug. 2012, now U.S. Pat. No. 8,684,734, which is a continuation-in-part of U.S. patent application having Ser. No. 13/195,872 filed on 2 Aug. 2011, now U.S. Pat. No. 8,297,974, which is a continuation of U.S. patent application having Ser. No. 11/358,375 filed on 21 Feb. 2006, now U.S. Pat. No. 8,043,090, which is a continuation of U.S. patent application having Ser. No. 10/375,343 filed on 27 Feb. 2003, now U.S. Pat. No. 7,291,012, which are incorporated herein by reference.

BACKGROUND OF THE INVENTION

Much effort has been directed to integrating dental implants into surrounding bone. Ideally, a dental implant would be placed into alveolar bone, and thereafter bone would readily grow into the surface of the implant. To achieve this objective, many different surface technologies have been applied to dental implants. In some instances, the surface of the implant is roughened, grit-blasted, plasma-sprayed, or microtextured. In other instances, the surface is coated with a biological agent, such as hydroxylapatite (HA). In all of these instances, the goal is the same: Produce a surface on the dental implant into which surrounding bone will grow or bond.

Porous coatings have also been applied to surfaces of dental implants. U.S. Pat. No. 5,989,027 entitled: "Dental Implant Having Multiple Textured Surfaces" to Wagner et al. (and expressly incorporated herein by reference) teaches a dental implant having multiple textured surfaces on the same implant. One surface includes a porous coated substrate, and another surface includes a nonporous surface adapted to encourage bone growth or bonding.

Porous coatings are advantageous since bone will indeed grow into the surface of the implant. Osseointegration, to a limited extent then, has been achieved with porous coated surfaces. These surfaces though are far from ideal in terms of accepting and encouraging bone growth into the body of the implant.

Porous surfaces are often thin coatings applied to the metallic substrate of the implant. Bone surrounding the implant can only grow into the coating itself. Bone cannot grow through the coating and into the metallic substrate. The depth of bone growth into the implant is limited to the depth of the porous coating. Bone simply cannot grow completely through the implant.

SUMMARY OF THE INVENTION

One example embodiment is a dental implant with a coronal body that connects to a bone fixation body. The bone fixation body has a porous structure and also includes an internal cavity with a substance that stimulates bone growth. The porous structure extends through a center of the bone fixation body in a cross-sectional view of the bone fixation body.

DETAILED DESCRIPTION

Figure 1:
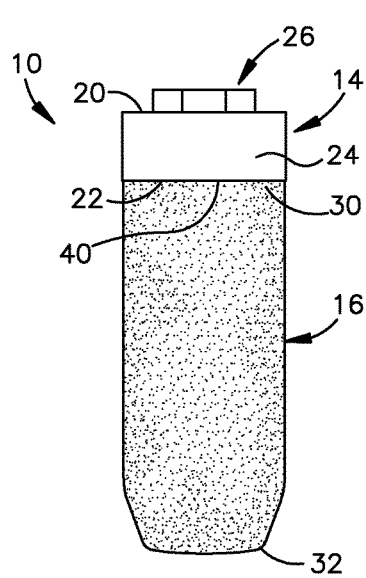
FIG. 1 is a side view of one embodiment of a dental implant.
Figure 2:
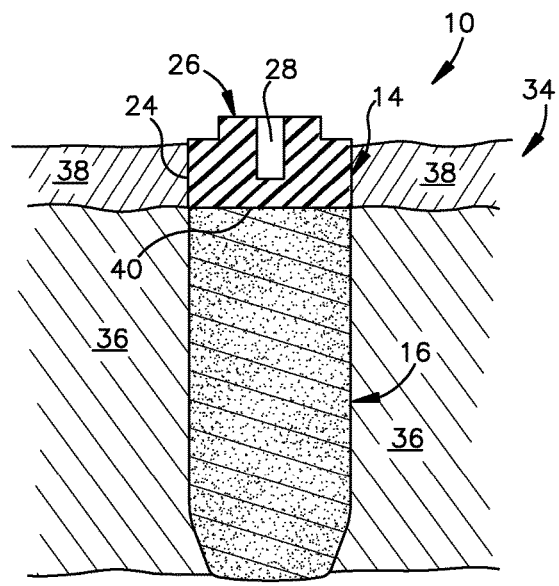
FIG. 2 is a cross-sectional view of the implant of FIG. 1 embedded in a jawbone of a patient.

Referring to FIGS. 1 and 2, an implant 10 is shown according to an example embodiment. Implant 10 is preferably constructed of a biocompatible material such as titanium and includes two primary components or bodies, a coronal body 14 and a bone fixation body 16.

The coronal body 14 has a short cylindrical configuration that extends from a proximal end surface 20 to a distal end surface 22. A transgingival section 24 is formed with a smooth outer surface. A dental interface 26 extends upwardly and adjacent the transgingival section. This interface (also referred to as an abutment-engaging end) is formed as a male hexagonal connector. The interface can have other embodiments, such as splines, internal and external octagons, stars, and other polygons. A threaded bore 28 extends into the coronal body and is adapted to receive a fixation screw for connecting the dental implant to a dental component, such as an abutment, prosthesis, healing collar, or the like. Preferably, the coronal body 14 is formed of a biocompatible metal, such as a solid metal piece of titanium or titanium alloy. The body can be machined to have a size and shape shown in the figures.

The bone fixation body 16 has an elongated cylindrical shape that extends from a proximal end 30 to a rounded distal end 32. Body 16 is formed from as a porous metal, such as titanium. Preferably, the body has a completely porous structure that extends throughout the entire body from the proximal to distal ends. Specifically, as shown in FIG. 2, body 16 does not include a metal substrate. The distal end surface 22 of coronal body 14 connects or fuses to the proximal end 30 of the bone fixation body 16 at a junction 40.

FIG. 2 shows the implant 10 embedded in a jawbone 34 of a patient. Preferably, the length of the body 16 extends along the region where the implant contacts surrounding bone 36 once the implant is implanted into the jawbone. The transgingival section 24 extends along the gum tissue or gingival tissue 38.

As noted, the bone fixation body 16 has a porous structure that extends from the outer surface and throughout the body. By "porous," it is meant that the material at and under the surface is permeated with interconnected interstitial pores that communicate with the surface. The porous structure can be formed by sintering titanium or titanium alloy powder, metal beads, metal wire mesh, or other suitable materials.

The porous structure of body 16 is adapted for the ingrowth of cancellous and cortical bone spicules. More particularly the size and shape of the porous structure emulates the size and shape of the porous structure of natural bone. Preferably, the average pore diameter of body 16 is about 40 μm to about 800 μm with a porosity from about 45% to 65%. Further, the interconnections between pores can have a diameter larger than 50-60 microns. In short, the geometric configuration of the porous structure should encourage natural bone to migrate and grow into and throughout the entire body 16.

Preferably, body 16 is created with a sintering process. One skilled in the art will appreciate that many variations exist for sintering, and some of these variations may be used to fabricate example embodiments. In a preferred embodiment, the coronal body is prepared using machining techniques. Next, a ceramic mold is provided. The mold has a first cavity that is sized and shaped to match the size and shape of the bone fixation body. In this first cavity, the sintering material can be placed. The mold also has a second cavity that is adjacent and connected to the first cavity. This second cavity is sized and shaped to receive the coronal body. The coronal body is positioned in the second cavity such that the distal end surface is adjacent and continuous with the first cavity.

The sintering material is then placed into the first cavity. This material may be a titanium alloy powder, such as Ti-6Al-4V. Some of this powder will contact the distal end surface of the coronal body. The mold is then heated to perform the sintering process. During this process, as the material in the first cavity heats and sinters, the bone fixation body forms and simultaneously bonds or fuses to the distal end surface of the coronal body.

The size and shape of the pores and porous structure produced in the first cavity depend on many factors. These factors include, for example, the temperature obtained in the furnace, the sintering time, the size and shape of sintering material, the composition of the sintering material, and the type of ceramic mold used. These factors (and others) can be varied to produce a bone fixation body in accordance with an example embodiment. Further, these factors (and others) can be varied to produce a strong bond between the bone fixation body and coronal body.

Once the sintering process is finished, the distal surface of the coronal body is directly fused to the bone fixation body. These two bodies are now permanently connected together to form the dental implant.

In the aforementioned sintering process, the bone fixation body simultaneously forms and attaches to the coronal body. One skilled in the art though will appreciate that each of these bodies can be fabricated independently and subsequently connected together. If the bodies are made separately, then they may be attached or fused together using welding or brazing techniques, for example.

Figure 3:
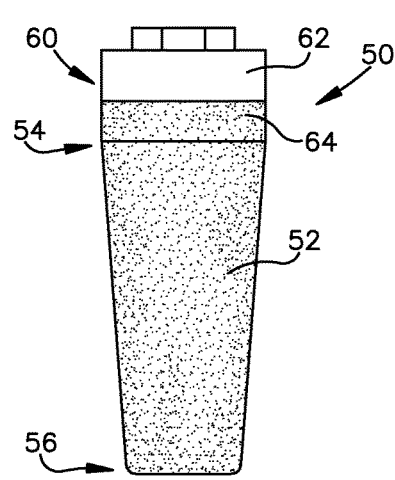
FIG. 3 is a side view of another embodiment of a dental implant.
Figure 4:
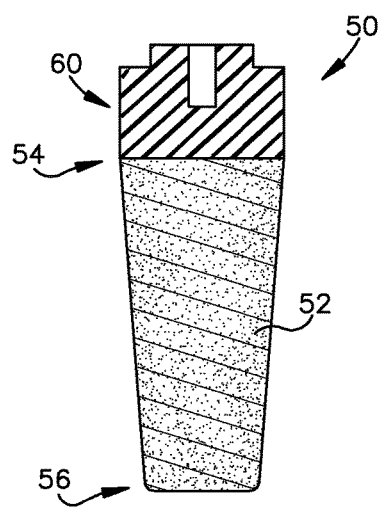
FIG. 4 is a cross-sectional view of FIG. 3.

FIGS. 3 and 4 show another implant 50 according to another example embodiment. With some differences, implant 50 is similarly configured to the implant 10. As one difference, the bone fixation body 52 has a gradual and continuous taper that extends from the proximal end 54 to the distal end 56. Further, the coronal body 60 has two different and distinct regions on the outer surface. A first region 62 has a smooth outer surface. A second region 64 has a bone-engaging surface that is contiguous and adjacent to the first region 62 on one side and contiguous and adjacent the porous bone fixation body 52 on the other side. The second region is non-porous and can be formed with various techniques. These techniques include, for example, coating with HA, grit-blasting, etching, micro-texturing, other non-porous surface treatments, or combinations of these techniques. This surface is provided as an intermediate zone between the porous body and the smooth first region 62.

Figure 5:
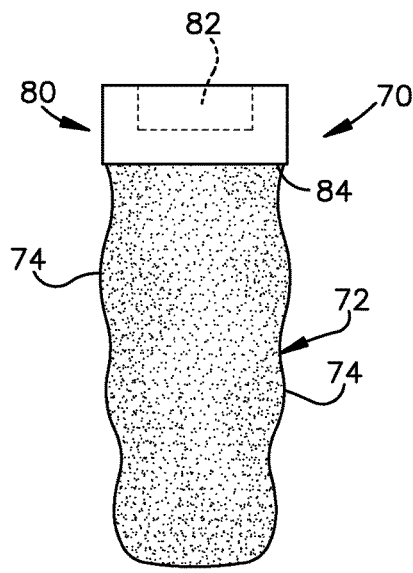
FIG. 5 is a side view of yet another embodiment of a dental implant.
Figure 6:
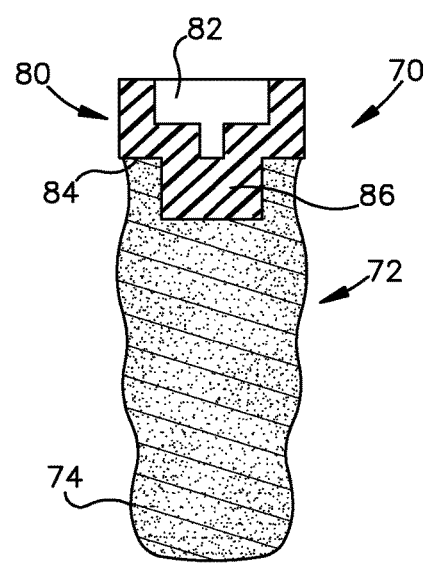
FIG. 6 is a cross-sectional view of FIG. 5.

FIGS. 5 and 6 show another implant 70 according to another example embodiment. With some differences, implant 70 is similarly configured to the implant 10. As one difference, implant 70 has a bone fixation body 72 with an outer surface that has a plurality of undulation 74, such as hills and valleys. These undulations are adapted to firmly secure the implant into the jawbone after the implant is placed therein. Further, the coronal body 80 has a dental interface 82 formed as an internal connection, such as an internal hexagon or other internal polygon. Further yet, the distal end surface 84 of the coronal body has an elongated protrusion 86 extending outwardly. This protrusion extends into the bone fixation body 72 and is adapted to increase the interface between the coronal body and bone fixation body. This protrusion may have various configurations, such as non-tapering, tapering, cylindrical, square, rectangular, hexagonal, octagonal, polygonal, or other shapes. Preferably, the protrusion is formed as a cylinder or square.

Figure 7:
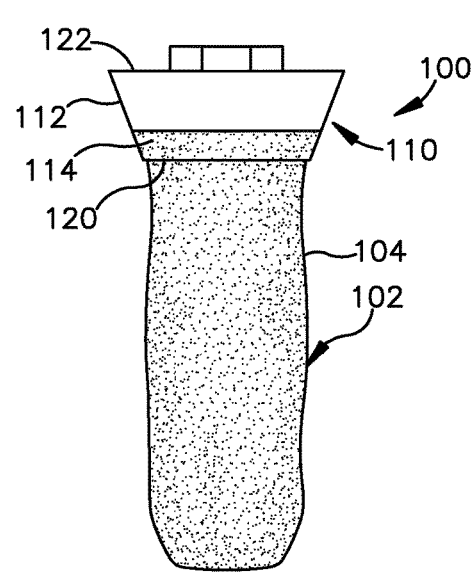
FIG. 7 is side view of another embodiment of a dental implant.
Figure 8:
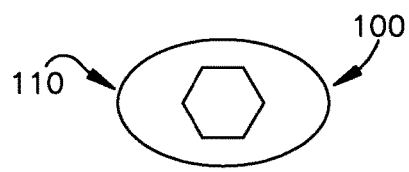
FIG. 8 is a top view of the FIG. 7.

FIGS. 7 and 8 show another implant 100 according to another example embodiment. With some differences, implant 100 is similarly configured to the implant 10. As one difference, implant 100 has a bone fixation body 102 with an uneven outer surface 104. This surface is adapted to aid in bone integration and anti-rotation between the bone fixation body and surrounding bone. Further, the coronal body 110 has two different and distinct regions on the outer surface. A first region 112 has a smooth outer surface; and a second region 114 has a bone-engaging surface. These regions are similar to the regions 62 and 64 described in connection with FIGS. 3 and 4.

As yet another difference, the coronal body 110 has a shape and size adapted to conform to the size and shape of natural teeth. The shape of this body is used, for example, in single-stage dental implants. The shape and size of the coronal body can thus contour the gingival or gum tissue to a natural shape that surrounds teeth. The size and shape, for example, can be similar to a molar, premolar, or incisor. FIG. 8 shows a top view of the coronal body 110 to have a shape of an oval or ellipse. As shown in FIG. 7, coronal body can taper upwardly from the distal end 120 to proximal end 122.

Figure 9:
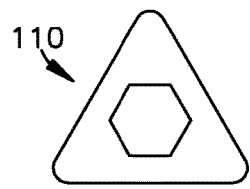
FIG. 9 is an alternate top view of FIG. 7.

FIG. 9 shows a top view of the coronal body 110 in an alternate embodiment to have a triangular shape.

The bone fixation body can be adapted to induce bone growth into and entirely through the body. The body, for example, can be doped with biologically active substances. These substances may contain pharmaceutical agents to stimulate bone growth all at once or in a timed-release manner.

Figure 10A:
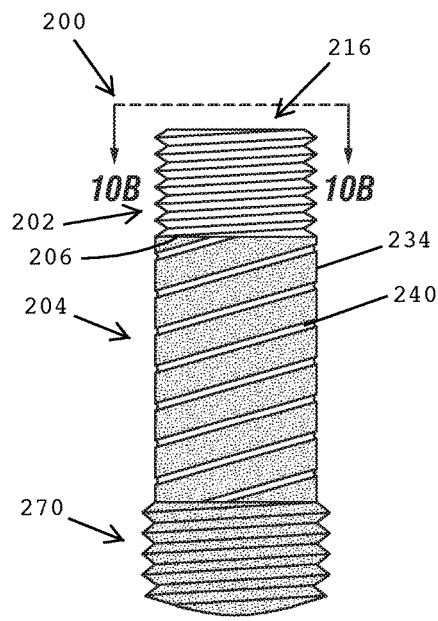
FIG. 10A is a side view of another example embodiment of a dental implant.
Figure 10B:
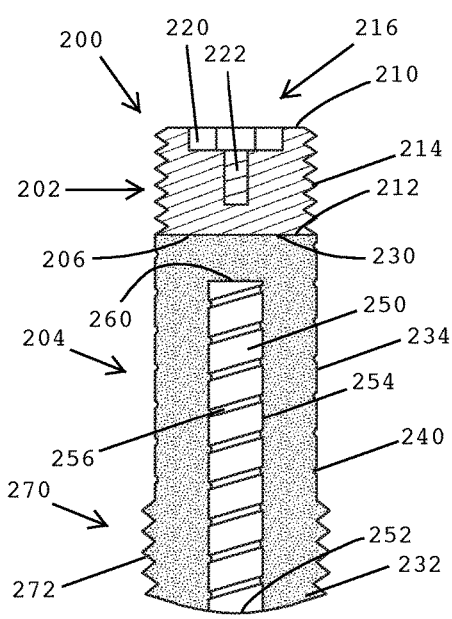
FIG. 10B is a cross-sectional view of FIG. 10A taken along lines 10B-10B.

FIGS. 10A and 10B show a dental implant 200 that includes a coronal body 202 and a bone fixation body 204. The coronal body 202 connects the bone fixation body 204 along an interface or juncture 206.

The coronal body 202 has a short cylindrical configuration that extends from a proximal end surface 210 to a distal end surface 212. External threads or grooves 214 extend along an exterior surface from the proximal end surface 210 to the distal end surface 212. A dental interface 216 extends inwardly into the coronal body 202. This interface includes a female hexagonal connector 220 and a threaded bore 222. The interface can have other embodiments, such as friction-fit connections, splines, internal polygons, and/or external polygons.

The dental interface 216 connects to another dental component, such as an abutment or a tooth-shaped prosthesis. For example, a tooth-shaped prosthesis has a distal end with a male hexagonal connector that fits into and engages with the female hexagonal connector 220. A screw extends from the tooth-shaped prosthesis and into the threaded bore 222 to connect the tooth-shaped prosthesis to the dental implant 200.

In one example embodiment, the coronal body 202 is formed of a biocompatible metal, such as a solid metal piece of titanium, titanium alloy, or other biocompatible metals and/or biocompatible materials. The external threads or grooves 214 are machined into the exterior surface of the coronal body 202 and include a micro-textured surface, such as a micro-textured surface created by grit-blasting with HA.

The bone fixation body 204 has an elongated cylindrical shape that extends from a proximal end 230 at the interface 206 to a distal end 232. An external surface 234 of the bone fixation body 204 includes threads, channels, and/or grooves 240 that extend from the proximal end 230 to the distal end 232. An internal cavity 250 is located inside the bone fixation body 204 and extends from a location adjacent the interface 206 to the distal end 232.

The internal cavity 250 forms a circular opening 252 at the distal end 232 of the bone fixation body 204. The internal cavity 250 has a cylindrical shape and is centrally located inside of the bone fixation body 204 such that the sides or wall 254 of the cavity are equally spaced from the external surface 234. The wall 254 includes grooves 256 that are formed in and spiral around the wall. These grooves 256 circumferentially extend around the wall 254 and form a continuous channel that extends from the circular opening 252 to an end surface 260 of the internal cavity 250.

While the dental implant 200 is being positioned into the jawbone of the patient, bone enters and fills the internal cavity 250. As the implant rotates and threads into the jawbone, bone is forced into the cavity and travels upwardly along the grooves 256 toward the end surface 260. The grooves guide and facilitate the passage of bone into the internal cavity. For example, bone travels in the grooves 256 from the opening 252 to the end surface 260 in order to fill the internal cavity 250.

Example embodiments are not limited to the grooves 256 spiraling around the wall 254. For example, the grooves can be straight and extend parallel to each other from the opening 252 to the end surface 260. Such grooves facilitate the transfer of bone into the cavity 250 while the dental implant 200 is being screwed, forced, or pressed into the jawbone. Alternatively, the cavity 250 can be formed without grooves.

The distal end 232 of the bone fixation body 204 includes a self-tapping end 270. This self-tapping end 270 includes one or more of recesses, channels, threads, and/or flutes that create cutting edges 272. These edges cut into bone and tissue as the implant is being placed into the jawbone. The recesses between the cutting edges also create pathways for holding and transporting bone and/or tissue displaced during insertion of the dental implant. Furthermore, these recesses align and/or communicate with the grooves 240 so bone can smoothly travel and flow from the self-tapping end 270, into grooves 240, and toward the coronal body 202.

Since the bone fixation body 204 is formed from a porous structure, the external grooves 240, the internal grooves 256, and the self-tapping end 270 are formed into the porous structure of the bone fixation body. Thus, the porous structure of the bone fixation body not only provides a structure for integrating with bone but also provides a surface to tap bone and move bone fragments.

As noted, the self-tapping end 270 is formed in the porous structure of the bone fixation body 204. For example, the self-tapping end is formed from the material of the porous structure and is integrally formed with the rest of the bone fixation body. FIG. 10B shows the porous structure of the self-tapping end 270 as being continuous with the remainder of the bone fixation body. Alternatively, the self-tapping end can include additional or different material (i.e., material not found in the remainder of the bone fixation body) to assist the distal end 232 in functioning to tap into the bone. For example, a coating is applied to the self-tapping end to provide additional strength to the porous structure at the end of the dental implant.

The grooves 240 spiral around the external surface 234 of the dental implant 200. These grooves 240 circumferentially extend around the external surface 234 and form a continuous channel that extends from the distal end 232 to the proximal end 230 at the interface 206. These grooves also align and/or communicate with the grooves 214 at the coronal body 202 so bone can smoothly travel and flow from the self-tapping end 270, into grooves 240, and into grooves 214. The grooves along the exterior surface of the dental implant thus facilitate the movement of bone from the distal end of the implant to the proximal end of the dental implant. Bone travels in the grooves and around the exterior surface to facilitate place of the dental implant and to assist in forming a secure mechanical attachment between the dental implant and surrounding bone and tissue.

Example embodiments are not limited to the grooves 240 spiraling around the exterior surface 234. For example, the grooves can be straight and extend parallel to each other from the opening 252 to the interface 206. Such grooves facilitate the transfer of bone along the exterior surface 234 while the dental implant 200 is being forced or pressed into the jawbone. Alternatively, the exterior surface 234 can be formed without grooves (for example, formed of the porous material but with a smooth exterior surface).

Figure 11A:
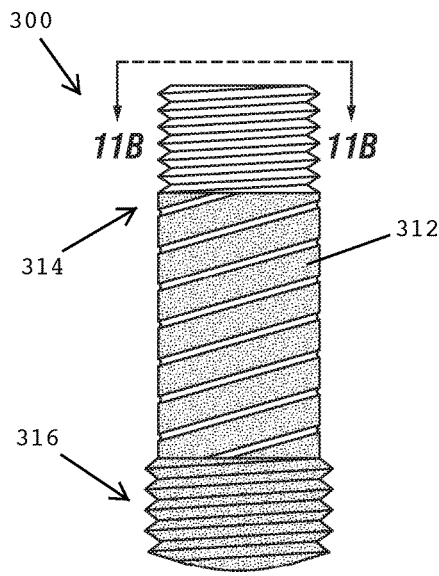
FIG. 11A is a side view of another example embodiment of a dental implant.
Figure 11B:
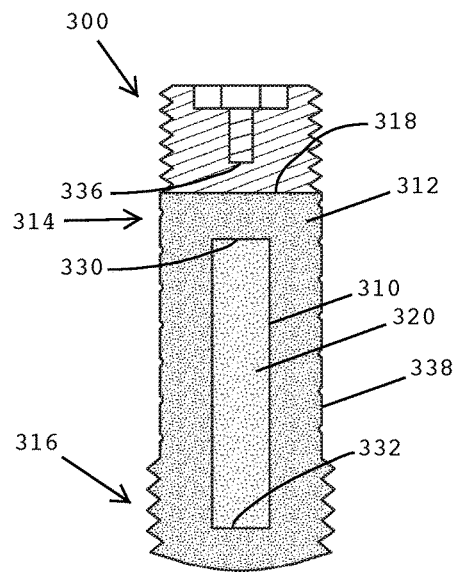
FIG. 11B is a cross-sectional view of FIG. 11A taken along lines 11B-11B.

FIGS. 11A and 11B show another dental implant 300 according to an example embodiment. With some differences, the implant 300 is similarly configured to the implant 200 in FIGS. 10A and 10B. As one difference, the implant 300 includes an internal cavity 310 that is enclosed within the bone fixation body 312. This cavity 310 has a cylindrical shape, extends from near or adjacent the juncture 318 at the proximal end 314 of the bone fixation body to near the distal end 316 of the bone fixation body, and is completely enclosed within the bone fixation body. In one example embodiment, the bone fixation body 312 completely surrounds the sides, the top, and the bottom of the cylindrically-shaped internal cavity 310 (i.e., the internal cavity is surrounded on all sides by the porous structure). As such, the internal cavity 310 lacks an ingress (such as a hole or a passageway) for entering the cavity or an egress for exiting the cavity (such as a hole or a passageway). Nonetheless, the open-celled configuration of the porous structure of the bone fixation body does allow bone to grow into and through the bone fixation body. Thus, the internal cavity can still communicate with the bone fixation body and with bone external to the bone fixation body through the interconnected interstitial pores to enable bone growth since the internal cavity is surrounded by and formed within an open-celled porous structure.

As shown in FIG. 11B, the internal cavity includes a substance 320 to cause or stimulate bone growth. This substance 320 fills the internal cavity 310 from a proximal end surface 330 of the internal cavity to an oppositely disposed distal end surface 332 of the internal cavity.

In one example embodiment, the substance 320 is trapped within the enclosed internal cavity. For example, the substance is placed in the internal cavity during manufacturing or formation of the dental implant. Alternatively, the substance is placed in the internal cavity after the dental implant is constructed. For instance, a small opening is formed through the implant, the substance is placed through the opening and into the internal cavity, and then the opening is sealed and/or closed. By way of example, an opening or hole is placed at the end of the screw cavity 336. This opening or hole provides temporary access to the internal cavity 310. After the substance is placed in the internal cavity, the opening or hole is closed. As yet another example, the substance is liquefied and forced through the interconnected interstitial pores of the bone fixation body and into the internal cavity. In this example, the substance travels from an exterior surface 338, through the bone fixation body 312, and into the internal cavity 310.

FIGS. 12A, 12B, 12C, and 12D show another dental implant 400 according to an example embodiment. With some differences, the implant 400 is similarly configured to the implant 300 in FIGS. 11A and 11B. As one difference, the implant 400 includes an internal cavity 410 that has a shape of a wheel enclosed within the bone fixation body 404. This internal cavity has a cylindrically shaped main body portion 420 with a plurality of spokes or channels 430 that extend outwardly from the main body portion 420. The main body portion and the spokes are surrounded and enclosed within the bone fixation body (for example, in a similar manner as the internal cavity is enclosed within the bone fixation body discussed in connection with FIGS. 11A and 11B).

Figure 12A:
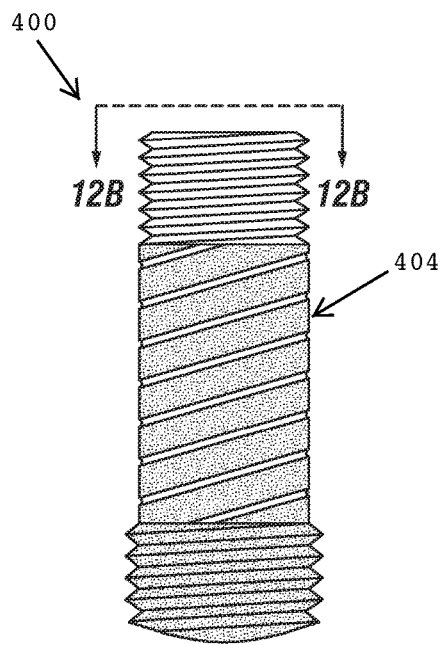
FIG. 12A is a side view of another example embodiment of a dental implant.
Figure 12B:
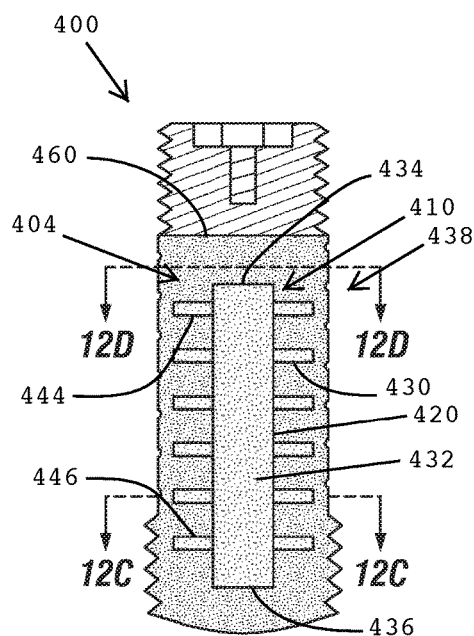
FIG. 12B is a cross-sectional view of FIG. 12A taken along lines 12B-12B.
Figure 12C:
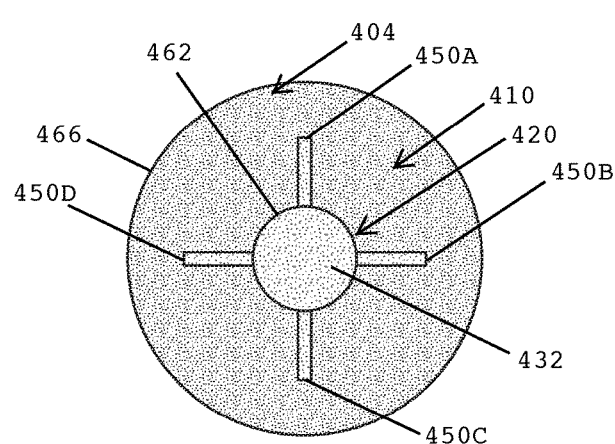
FIG. 12C is a cross-sectional view of FIG. 12B taken along lines 12C-12C.

As shown in FIGS. 12B and 12C, the internal cavity 410 includes a substance 432 to cause or stimulate bone growth. This substance 432 fills the internal cavity 410 from a proximal end surface 434 of the internal cavity to an oppositely disposed distal end surface 436 of the internal cavity. In one example embodiment, the substance 432 is trapped within the internal cavity.

FIG. 12B shows a series of sets of spokes 438 that are stacked on top of each other inside the bone fixation body 404. Six sets of spokes are vertically arranged in the bone fixation body. These sets of spokes are evenly spaced apart from each other and extend outwardly from the main body portion 420. A first set of spokes 444 is located near the proximal end 434 of the internal cavity, and a sixth set of spokes 446 is located near the distal end 436 of the internal cavity.

FIG. 12C shows that each set of spokes includes four spokes 450A, 450B, 450C, and 450D that are evenly spaced from each other and radiate outwardly from the main body portion 420. These spokes are in fluid communication with each other, with the other spokes in the other sets, and with the main body portion such that the substance 432 located inside the cavity can flow or migrate among the sets of spokes and the main body portion. As discussed herein, the substance, however, is not limited to being a fluid, but can be a solid structure, such as a scaffold, a membrane, a powder, a metal, and/or a polymer.

FIG. 12C also shows that the internal cavity 410 is centrally located in the bone fixation body 404. An exterior wall 462 of this internal cavity is equally spaced from an exterior wall 466 of the bone fixation body 404.

The sets of spokes facilitate the dispersement and growth of bone throughout the bone fixation body 404. Specifically, the sets of spokes are filled with the substance 432, and this substance causes and/or encourages bone to grow from and into the sets of spokes and surrounding areas of the bone fixation body. The sets of spokes assist in dispersing the substance 432 into a larger volume or area of the bone fixation body since these spokes radiate throughout the bone fixation body.

Figure 12D:
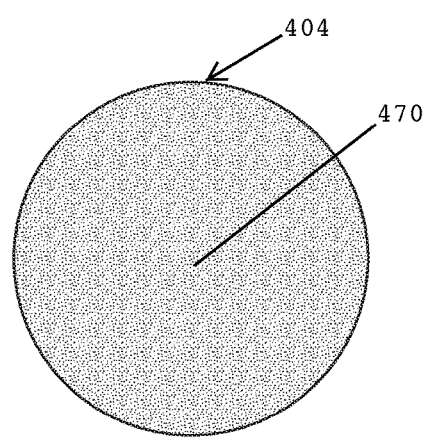
FIG. 12D is a cross-sectional view of FIG. 12B taken along lines 12D-12D.

FIG. 12D shows a cross-section of the dental implant taken adjacent the interface 460. As shown, the porous structure continuously extends through an entire cross-sectional view of the bone fixation body at this location such that the porous structure includes a center 470 of the bone fixation body in the cross-sectional view. Thus, in this view, the porous structure completely fills the cross-section of the dental implant.

Figure 13:
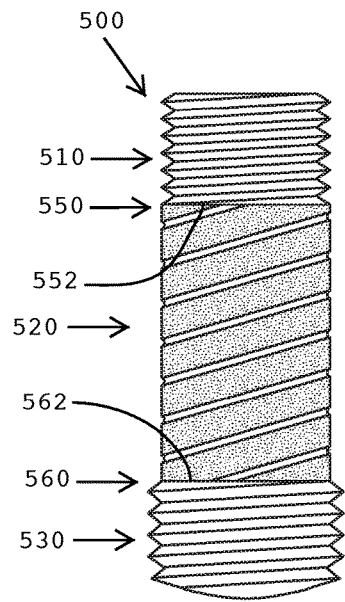
FIG. 13 is a side view of another example embodiment of a dental implant.

FIG. 13 shows another dental implant 500 according to an example embodiment. With some differences, the exterior configuration of this implant is similar to the exterior configuration of the dental implant 200 shown in FIG. 10A. As one difference, the dental implant 500 has three separate sections that include a coronal body 510, a bone fixation body 520, and a self-tapping body 530. The bone fixation body 520 has a structure and/or is formed of a material that is different than the coronal body 510 and the self-tapping body 530. For example, the bone fixation body 520 has a porous structure, while the coronal body 510 and the self-tapping body 530 have a non-porous structure (e.g., formed of solid titanium or titanium alloy with a roughened or porous surface).

In the example embodiment of FIG. 13, the bone fixation body 520 is positioned between the coronal body 510 and the self-tapping body 530. A proximal end 550 of the bone fixation body connects to the coronal body 510 along an interface 552, and a distal end 560 connects to the self-tapping body 530 along an interface 562. At the interfaces 552 and 562, the bone fixation body has a circular cross-section with the porous structure completely filling this cross-section (for example, as shown in the circular cross-section in FIG. 12D). These circular cross-sections of the bone fixation body connect to solid metal circular cross-sections of the coronal body 510 and the self-tapping body 530.

The coronal body 510 and the self-tapping body 530 are structurally stronger than the bone fixation body 520 since they are formed to have a non-porous structure whereas the bone fixation body is formed to have a porous structure. As such, the bone fixation body is configured so that bone can grow completely through the porous structure. By contrast, the coronal body and the self-tapping body are configured so that bone can grow into an outer surface but not into and through center of the bodies since these locations are filled with solid metal. For example, the outer surfaces of coronal body and the self-tapping body are micro-textured or covered with a porous structure. These surfaces can integrate with surrounding bone after the dental implant is implanted in the jawbone.

The dental implant 500 can have different interior configurations. In one example embodiment, the dental implant 500 is configured with an internal cavity as shown in FIG. 10B (see internal cavity 250 shown in FIG. 10B). As another example embodiment, the dental implant 500 is configured with an internal cavity as shown in FIG. 11B (see internal cavity 310 in FIG. 11B). As another example embodiment, the dental implant 500 is configured with an internal cavity as shown in FIG. 12B (see internal cavity 410 in FIG. 12B).

Figure 14:
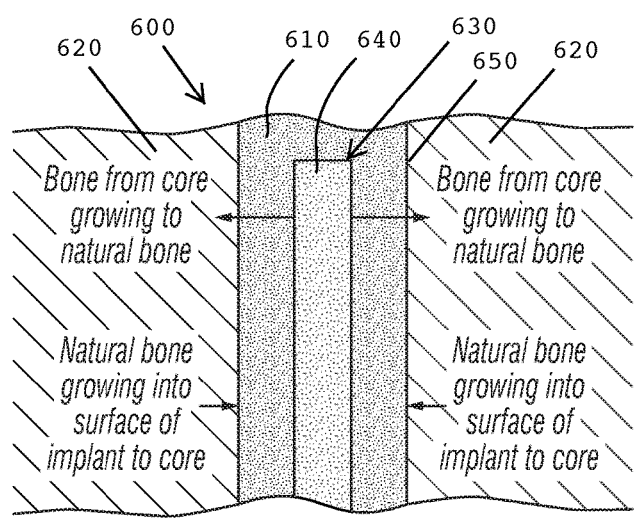
FIG. 14 is a partial cross-sectional view of a dental implant embedded in a jawbone of a patient.

FIG. 14 is a partial cross-sectional view of a dental implant embedded in a jawbone of a patient. For example, this cross-section can represent the proximal end of the bone fixation body 204 of implant 200 shown in FIG. 10B. As another example, this cross-section can represent the proximal end of the bone fixation body 312 of the implant 300 shown in FIG. 11B. As yet another example, this cross-section can represent the proximal end of the bone fixation body 710 of the implant 700 shown in FIG. 15.

As shown in FIG. 14, the dental implant 600 includes a bone fixation body 610 that is embedded in a jawbone 620 of a patient. This bone includes cortical bone and/or cancellous bone. The bone fixation body 610 includes an internal cavity 630 that is filled with a substance 640 to cause or stimulate bone growth.

Once the dental implant 600 is implanted into the jawbone 620, bone simultaneously begins to grow with natural bone growing inwardly toward the internal cavity 630 and bone from the substance growing outwardly from the internal cavity 630 toward the natural bone 620 that is growing inwardly. Natural bone 620 surrounding the dental implant 600 begins to grow into the outer surface 650 of the bone fixation body 610. At the same time, bone begins to grow outwardly from the internal cavity 630 and toward the outer surface 650. The substance causes or stimulates bone to grow outwardly from the internal cavity.

The porous structure of the bone fixation body thus supports bone growth inwardly toward the center of the implant and outwardly away from the center of the implant. Thus, bone grows from two different and separately located sources (one source being the natural bone located outside of the dental implant and a second source being the substance 640 located inside of the dental implant). This process of concurrently growing bone from two different locations (i.e., from within the implant and from outside of the implant) decreases the time required for bone to grow throughout the dental implant including the center of the dental implant where the substance is located. For example, the time required for bone to grow from one side of the bone fixation body to an oppositely disposed side of the bone fixation body is reduced since bone is concurrently growing both toward the center of the bone fixation body and outwardly from this center immediately after the dental implant is implanted into the jawbone. This process also decreases the time required for bone to completely fill the porous structure of the bone fixation body since bone grows in multiple different directions. For instance, bone simultaneously grows in directions from the internal cavity through sides of the cavity, through the top of the cavity, and through the bottom of the cavity. Additionally, bone grows through the sides and the bottom of the exterior surfaces of the bone fixation body. The dental implant is thus able to more quickly fully integrate with bone after being implanted (for example, more quickly have bone grow throughout the entire structure of the bone fixation body). Growing bone from the center of the implant thus expedites the time required to complete the bone integration process.

Figure 15:
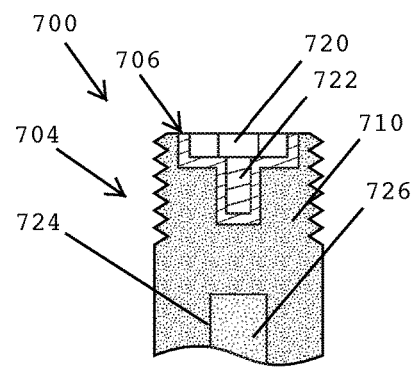
FIG. 15 is a partial cross-sectional view of a coronal end of another example embodiment of a dental implant.

FIG. 15 is a partial cross-sectional view of another example embodiment of a dental implant 700. A proximal or coronal end 704 of this dental implant includes a metal dental interface 706 that is surrounded by a bone fixation body 710 having a porous structure.

The dental interface 706 extends inwardly into the bond fixation body 710. This interface includes a female hexagonal connector 720 and a threaded bore 722 that engages with a screw. The interface can have other embodiments, such as friction-fit connections, splines, internal polygons, and/or external polygons.

The bone fixation body 710 includes an internal cavity 724 with a substance 726 to cause or stimulate bone growth. The configuration of the bone fixation body 710 below the dental interface 706 can vary. As one example, the configuration of the bone fixation body 710 below the dental interface 706 of FIG. 15 is shown in FIGS. 10A and 10B with bone fixation body 204, internal cavity 250, and other aspects shown in these figures. As another example, the configuration of the bone fixation body 710 below the dental interface 706 of FIG. 15 is shown in FIGS. 11A and 11B with bone fixation body 312, internal cavity 310, and other aspects shown in these figures. As another example, the configuration of the bone fixation body 710 below the dental interface 706 of FIG. 15 is shown in FIGS. 12A-12C with bone fixation body 404, internal cavity 410, and other aspects shown in these figures.

The dental interface 706 is formed of a biocompatible metal, such as a solid metal piece of titanium, titanium alloy, or other biocompatible metals and/or materials. By contrast, the bone fixation body 710 is formed of a porous structure. This dental interface is embedded or disposed in the porous structure.

In one example embodiment, the porous structure completely surrounds the exterior surface of the dental implant from its proximal end to its distal end. Since this porous structure also surrounds the proximal or coronal end 704 of the dental implant, bone can grow into the entire exterior surface area of the dental implant at the coronal end. For example, when the dental implant includes one of the configurations of the bone fixation body 710 below the dental interface 706 discussed herein (such as shown in FIGS. 10A, 10B, 11A, 11B, 12A, and 12B), then bone can grow into the entire outer surface of a porous structure of the dental implant. The implant in such embodiments does not include a non-porous outer surface. The implant in such embodiments, however, would include a solid metal coronal body that is embedded into the porous structure of the bone fixation body.

In an example embodiment, the porous structure of the bone fixation body is different than the structure of the substance located in the internal cavity in the bone fixation body. The geometry and material composition of the porous structure of the bone fixation body and the substance in the internal cavity both induce bone formation throughout the internal cavity and the bone fixation body. The geometry and material composition of the porous structure of the bone fixation body, however, also provides strength to the implant since it bears loads from mastication forces on the tooth prosthesis. A majority of these loads pass along the bone fixation body and not to the substance located in the internal cavity. As such, the geometry and material composition of the substance can be for stimulating bone growth, whereas the geometry and material composition of the bone fixation body can be for stimulating bone growth and providing strength to the dental implant.

By way of example, the substance includes a porous structured scaffold that is inserted or fabricated in the internal cavity of the bone fixation body. This scaffold has a geometry and material composition to induce bone growth through the internal cavity and into the surrounding walls of the bone fixation body. This scaffold would not have to support the mastication loads since the bone fixation body surrounding the internal cavity supports these loads. Alternatively, the geometry and material composition of the substance located in the internal cavity can also be for providing strength to the dental implant.

In an example embodiment, the substance in the internal cavity is activated when the implant is placed into the jawbone of the patient. As one example, looking to FIG. 10B, the substance is located in the internal cavity 250. While the dental implant 200 is being placed into the jawbone, bone, tissue, blood, and other substances come in contact with the substance in the internal cavity and activate this substance to begin stimulating bone growth in the internal cavity. As another example, looking to FIG. 11B, while the dental implant 300 is being placed into the jawbone, a fluid (including one or more of bone, tissue, blood, and other substances created from the implantation procedure) seeps or passes through the porous structure of the bone fixation body 312 and comes in contact with the substance 320 in the internal cavity 310. This fluid activates this substance 320 to begin stimulating bone growth in the internal cavity 310. Alternatively, bone growth and bone stimulation properties of the substance are activated with an agent (for example, an external agent applied to the structure and/or the substance during implantation).

FIGS. 10B, 11B, and 12B show the dental implant with an internal cavity. The size and shape of this internal cavity can vary depending on, for example, the size and shape of the dental implant, the substance included in the internal cavity, the mechanical properties desired for the implant, and the material used to fabricate the porous structure. By way of example, these shapes of the internal cavity include, but are not limited to, cylinders (such as right circular cylinders having a cross-section as a circle, elliptic cylinders having a cross-section as an ellipse, hyperbolic cylinders having a cross-section as a hyperbola, parabolic cylinders having a cross-section as a parabola, oblique cylinders having top and bottom surfaces displaced from each other, and tapered cylinders), cones (such as right cones, oblique cones, truncated cones, and elliptical cones), wheels, spheres, cuboids, polyhedrons, polytopes, pyramids, linear and non-linear tunnels and pathways, symmetric and asymmetric voids and cavities, three dimensional shapes (such as shapes having curved lines, straight lines, closed configurations, and/or open configurations), and combinations of these shapes.

Additionally, the size and shape of the internal cavity can be adjusted to provide a closer biomechanical match of strength, stiffness, and architectural structure between the dental implant and the surrounding bone. The combination of pores in the porous structure and space of the internal cavity reduces the overall stiffness values of the dental implant so it can more closely resemble the stiffness values and properties of natural bone.

FIGS. 2, 4, 6, 10B, 11B, and 12B show that the porous structure of the bone fixation body connects to the metal coronal body at an interface that has a circular or elliptical cross-section (the particular cross-sectional shape of this interface depends on the shape of the bone fixation and coronal bodies and includes shapes other than circular or elliptical). For example, if the bone fixation body and the coronal body are both formed as right cylinders at the juncture of their interface, the interface (when viewed in a cross-section) is circular. Such an interface includes the entire volume of this circular cross-section since the circular cross-section of the bone fixation body abuts the circular cross-section of the coronal body. This abutment of two circular cross-sections (or other shaped cross-sections) provides strength to the implant at the juncture where the non-porous structure of the coronal body connects to the porous structure of the bone fixation body.

FIGS. 2, 4, 6, 10B, 11B, 12B, 13, and 15 show that a bone fixation body with a porous structure connects to a coronal body with a non-porous structure (for example, the coronal body has as a solid metal structure formed of titanium or titanium alloy). The structure of the coronal body is thus stronger than the structure of the bone fixation body. The coronal body is formed of a non-porous structure to provide strength to the dental implant and structural support for the porous structured bone fixation body. This added strength is useful since mastication forces transfer from the tooth prosthesis to the dental implant at the coronal body. Alternatively, the coronal body can be formed of a porous structure, but this porous structure should be strong enough to endure the mastication forces encountered at the coronal end of the dental implant.

The substance to cause or stimulate bone growth can be formed from a variety of different materials and different processes. As one example, the substance includes a mixture of one or more bone morphogenetic proteins (BMPs) and one or more carriers. For instance, this mixture includes BMP 4, collagen, and a polymer, such as poly (lactic-co-glycolic acid) (PLGA) or poly (L-lactide) (PLLA). As another example, the substance includes one or more of natural bone and/or tissue and/or blood from the patient receiving the implant, tantalum, an acrylate based polymer, biphasic calcium phosphate (BCP), carboxymethylcellulose (CMC), hydroxypropylmethylcellulose (HPMC), hydroxyapatite (HA), tricalcium phosphate (TCP), stem cells (including human embryonic stem cells and adult stem cells), human bone-derived cells (hPBDs), biodegradable polymers (such as poly (glycolic acid) (PGA) and poly (lactic acid) (PLA)), poly($\alpha$-hydroxy acids), calcium-phosphates (CaP) (such as $\beta$-tricalcium phosphate ($\beta$-TCP) and $\alpha$-tricalcium phosphate ($\alpha$-TCP)), poly(D,L-lactide) (PDLLA), injectable bone (for example, injectable bone that includes calcium phosphate and/or calcium sulphate), allotransplantation (i.e., bone and/or tissue from a same species, such as allografts and autografts), xenotransplantation (i.e., bone and/or tissue from another species), rattan wood, bioactive glasses (such as a bioactive glass foam scaffold), cancellous structured titanium, resorbable porous structures, class A and class B bioactive materials, bone grafts, and other materials that cause and/or stimulate bone growth.

Furthermore, the substance can be formed with various geometric configurations, such as including one or more of a liquid, a powder, and a solid. These configurations include both porous structures and non-porous structures. By way of example, the substance is formed into a three-dimensional porous scaffold and placed in the internal cavity (for example, PGA, PLA, and/or PLGA scaffolds). The pore size and porosity of the scaffold can be optimized to induce colonization and proliferation of cells. For example, the pore sizes range from about 150 μm-700 μm), and the porosity of the scaffold ranges from about fifty percent (50%) to ninety percent (90%).

As discussed herein, the porous structure of the substance and/or the bone fixation body can be formed from a variety of different materials and different processes. As one example, the porous structure is formed from one or more of polymers, ceramics, and biocompatible metals and metal alloys. For example, the porous structure is constructed with tantalum, titanium, a titanium (Ti) alloy, such as titanium with one or more of zirconium (Zr), niobium (Nb), tin (Sn), silicon (Si), molybdenum (Mo), and tantalum (Ta)), biocompatible polymer, and/or a biocompatible metal or metal alloy.

By way of example, the porous structure is formed from one of a casting process and/or a powder metallurgy process. The casting process can include one or more of vacuum melting and annealing, hot rolling, scale removal, machining, and surface preparation. The powder metallurgy process can include one or more of a pre-alloying process (such as fabricating alloyed powder using gas atomization and melting) and a blending of metals to obtain a predetermined alloy composition. Metal powder is then cold pressed into a shaped and sintered. The porous structure can also be fabricated using one or more of sintering, casting, plasma-spraying, sputter deposition techniques, and metallic deposition techniques.

As another example, the porous structure is formed by coating a solid skeleton or a hollow skeleton with one or more of a polymer, a metal, and/or a metal alloy. For example, a carbon skeleton is coated with tantalum using a vapor deposition process. For instance, tantalum is deposited on a vitreous carbon foam structure.

As yet another example, the porous structure is formed from a metal injection molding (MIM) process. For example, metals and/or polymers are mixed to form a feedstock that is then shaped. The polymer is then removed, and the structure is heated, machined, and coated.

Furthermore, the porous structure can include opens cells (i.e., pores connected to each other through channels, voids, interstices, etc.), closed cells (i.e., pores disconnected from each other), and combinations of open and closed cells.

Additionally, the porosity of the porous structure can be constant throughout the porous structure or change within the porous structure. For instance, the porous structure can have a gradient porosity in which the porosity changes from the surface of the bone fixation body to the center of the bone fixation bode (for example, the porosity near the surface of the bone fixation body is different than the porosity inside the internal cavity).

The porosity can also increase or decrease at different locations along the dental implant. For instance, the porosity of the porous structure where the bone fixation body contacts cortical bone can be different than the porosity where the bone fixation body contacts cancellous bone. The porosity of the porous structure where the dental implant contacts cortical bone can be lower than the porosity of the porous structure where the dental implant contacts cancellous bone. Looking to FIG. 15 for example, the coronal body 704 where the dental implant 700 contacts cortical bone has a different porosity than where the bone fixation body 710 contacts cancellous bone (e.g., locations along the bone fixation body below the coronal body). Thus, the bone fixation body 710 can have a first porosity at the coronal end and a second, different porosity at other locations, such as below the coronal end and/or in the internal cavity 724.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. A method, comprising:
   machining a coronal body of a dental implant from solid metal to have a cylindrical configuration with a proximal end surface having an internal polygonal connection that connects to a dental component, with a distal end surface, and with an elongated cylindrical protrusion that extends outwardly from the distal end surface and includes a polygonal external shape in a side-view of the coronal body;
   fabricating, separately from the coronal body, a bone fixation body of the dental implant that has a cylindrical shape from a side-view of the bone fixation body and is formed of a porous metal structure without a metal substrate but with the porous metal structure that extends throughout the bone fixation body such that the porous metal structure includes interconnected interstitial pores including a porosity of 45% to 65% with a geometric configuration that encourages natural bone to migrate and grow into and throughout the porous metal structure; and
   connecting, after the bone fixation body is separately fabricated from the coronal body to have the cylindrical shape from the side-view, the bone fixation body to the coronal body to form the dental implant, the bone fixation body and the coronal body connecting at an interface where a proximal end surface of the bone fixation body abuts the distal end surface of the coronal body and where the elongated cylindrical protrusion of the coronal body extends into and engages the bone fixation body such that the bone fixation body surrounds and abuts the polygonal external shape of the elongated cylindrical protrusion in order to increase the interface between the coronal body and the bone fixation body.

2. The method of claim 1, wherein the porous metal structure has a size and a shape of a porous structure of natural bone.

3. The method of claim 1, wherein the elongated cylindrical protrusion of the coronal body has a non-tapering cylindrical shape.

4. The method of claim 1, wherein the dental implant includes three different regions of a smooth outer surface at a proximal end on the coronal body, the porous metal structure of the bone fixation body, and a non-porous bone engaging surface on the coronal body that is intermediate the smooth outer surface and the porous metal structure of the bone fixation body.

5. The method of claim 1, wherein the bone fixation body is bonded to the coronal body after the bone fixation body is separately formed from the coronal body.

6. The method of claim 1, wherein the cylindrical shape of the bone fixation body tapers in the side-view of the bone fixation body.

7. The method of claim 1, wherein the coronal body from the proximal end surface to the distal end surface has a non-tapering cylindrical shape in the side-view of the coronal body.

\* \* \* \* \*